United States Patent [19]

Iwasa et al.

[11] Patent Number: 5,506,135

[45] Date of Patent: Apr. 9, 1996

[54] HYBRID MONOCLONAL ANTIBODIES, THEIR PRODUCTION AND USE

[75] Inventors: Susumu Iwasa, Kyoto; Tomofumi Kurokawa; Yukio Toyoda, both of Hyogo, all of Japan

[73] Assignee: Takeda Chemical Industries, Ltd., Osaka, Japan

[21] Appl. No.: 366,366

[22] Filed: Dec. 29, 1994

Related U.S. Application Data

[63] Continuation of Ser. No. 9,412, Jan. 27, 1993, abandoned, which is a continuation of Ser. No. 412,903, Sep. 26, 1981, abandoned.

[30] Foreign Application Priority Data

Sep. 27, 1988 [JP] Japan .................................. 63-243544
Nov. 28, 1988 [JP] Japan .................................. 63-301925
Mar. 14, 1989 [JP] Japan .................................. 1-62940
Jun. 27, 1989 [JP] Japan .................................. 1-64873
Aug. 11, 1989 [JP] Japan .................................. 1-208936

[51] Int. Cl.$^6$ ............................ C12N 5/18; C07K 16/46; C07K 16/36; C07K 16/40
[52] U.S. Cl. ................................ 435/240.27; 530/373.3; 530/387.1; 530/391.3; 530/388.25; 530/388.26
[58] Field of Search ............................ 530/387.3, 387.1, 530/391.3, 388.25, 388.26; 435/240.27

[56] References Cited

U.S. PATENT DOCUMENTS 4,474,893 10/1984 Reading .................................. 436/547
4,714,681 12/1987 Reading .................................. 436/240.27
4,916,070 4/1990 Matsueda et al. .................... 435/172.2

FOREIGN PATENT DOCUMENTS

83/03679 2/1983 WIPO.
WO-A-8706240 10/1987 WIPO.

OTHER PUBLICATIONS

Molecular Immunology, 20, 521 (1983).
Proc. Natl. Acad. Sci. USA, 84, 7659 (1987).
Science, 229, 765 (1985), Bode et al.
Mountain et al. Biotechnology and Genetic Engineering Reviews. pp. 10–13 1992.
Goding. Monoclonal Antibodies Principles and Practice. 1986, p. 124.
Hird et al. Genes and Cancer 1990 p. 184.
Waldmann Science vol. 252:1657 1991.
PNAS Salemo et al. 81(1) 110–4 1984 (abstract).
Collen et al. Annu. Rev. med. 39 405–23 1988 (abstract).

*Primary Examiner*—Lila Feisee
*Attorney, Agent, or Firm*—David G. Conlin; Linda M. Buckley

[57] ABSTRACT

The present invention provides a hybrid monoclonal antibody having specificities against fibrin and thrombolytic substance, a polydoma which produces said antibody and thrombolytic agent comprising said antibody and thrombolytic substance which is immunologically coupled thereto, and methods of using said antibody in combination with thrombolytic substance for lysis or removal of thrombi.

3 Claims, 8 Drawing Sheets

TPA (μg/mℓ)

Fig. 7

Liberated peptide concentration (μg/mℓ)

HYBRID MONOCLONAL ANTIBODIES, THEIR PRODUCTION AND USE

This is a continuation Ser. No. 08/099,412 filed on Jan. 27, 1993 now abandoned which is a continuation for application Ser. No. 07/412,907 filed on Sep. 26, 1989, now abandoned.

BACKGROUND OF THE INVENTION

The present invention relates to a hybrid monoclonal antibody. More specifically, the present invention relates to a hybrid monoclonal antibody (hereinafter also simply referred to as hybrid MoAb) having specificities against fibrin and thrombolytic substance and a polydoma which produces said antibody.

The present invention also relates to a thrombolytic agent comprising the above hybrid MoAb and a thrombolytic substance which is immunologically coupled thereto.

Thrombolytic therapy has long been used to treat thrombotic diseases such as myocardial infarction, arterial embolism and cerebral infarction; initially, streptokinase (hereinafter also abbreviated SK), urokinase (hereinafter also abbreviated UK) etc. were clinically applied as efficient thrombolytic agents. Particularly, UK has been relatively commonly used since its fibrinolytic action is strong; however, it is faulty in that its selectivity for fibrin is low and that it acts on fibrinogen as well, and thus it causes a tendency toward bleeding in subject patients. In view of this drawback, tissue plasminogen activator (hereinafter also abbreviated TPA) and prourokinase (hereinafter also abbreviated ProUK) became used as second generation thrombolytic agents. With higher selectivity for fibrin in comparison with UK, these agents were expected to mitigate the adverse effect, i.e., a tendency toward bleeding, of UK; many investigations have so far been made. In recent years, there have been an increasing number of attempts to apply these agents in clinical situations since their massproduction has become possible by use of gene recombination technology [European Cooperative Study Group for Recombinant Tissue-type Plasminogen Activator: The Lancet, 842 (1985)].

These attempts at clinical application, however, revealed that TPA etc. also have some drawbacks; for example, ① TPA has a very short half life (2 to 3 minutes), thus requiring large-amount long-term administration for thrombolysis, and ② such high-dose therapy does not always provide a mitigating effect on the tendency toward bleeding.

Under these conditions, more effective thrombolytic agents were investigated and developed; modified TPA, UK-TPA or ProUK-TPA hybrid protein etc. have been produced. As to modified TPA, a TPA mutein lacking part of the sugar chain structure, which is considered a cause of the decrease in half life, has been prepared by gene engineering so that the capture of TPA by sugar-chain receptors of hepatocytes is avoided to improve TPA kinetics in blood. As to UK-TPA hybrid protein, the strong thrombolytic action of UK and the fibrin affinity of TPA are utilized in combination to reduce the administration amount. Although these thrombolytic agents are expected to slightly mitigate the tendency toward bleeding in comparison with conventional thrombolytic agents, significant improvement remains to be achieved by further research and development.

Later, protein complexes based on antibody targeting appeared as third generation thrombolytic agents. That is, thrombolytic agents which lyse fibrin alone without lysing fibrinogen were developed by chemically binding an antibody which does not substantially react on fibrinogen and which possesses high affinity with fibrin alone to UK [C. Bode et al.:. Science, 229, 765 (1985)] or TPA [M. S. Runge et al.: Proceedings of the National Academy of Science, USA, 84, 7659 (1987)]. These antibody-targeting thrombolytic agents are all reported to have exhibited an effect 3 to 100 times stronger than that of simple UK or TPA in experiments in vitro or in vivo. These protein complexes, however, all have drawbacks due to the chemical binding of an antibody and a thrombolytic enzyme; for example, ① the antibody activity and enzyme activity decrease during the chemical binding procedure, ② it is difficult to obtain a protein complex of antibody and enzyme in a ratio of 1 to 1, or ③ protein denaturation accelerates the agent's metabolism in the subject patient's body.

BRIEF DESCRIPTION OF THE DRAWING

FIG. 5 shows the amount of the bi-specific antibody FT 2-14 prepared in Example 4-③ bound to a fibrin-coupled paper disk. In FIG. 5, ■ shows the results obtained in the presence of fibrinogen (3 mg/ml ); □ shows the results obtained in the absence of fibrinogen (see Example 6).

FIGS. 12 A–F show the dilution curves respectively of JK 1-3, 1-87 and 1-6, prepared via the EIA procedure described in Reference Examples 3 and 10 (see Examples 3, 12 and 14). FIG. 12 A–C shows the reactivity to UK; FIGS. 12 D–F show the reactivity to low molecular weight UK.

FIGS. 13 A–C show the enzyme activity inhibition curves respectively of anti-UK monoclonal antibodies UK 1-3, 1-87 and 1-6 obtained by the UK enzyme activity neutralization test described in Reference Example 11 (see Examples 3, 12 and 15).

DETAILED DESCRIPTION

With the aim of solving the above problems related to in vivo metabolism, fibrin affinity, thrombolytic capability etc., and taking note of the recently developed new technology for bi-specific hybrid monoclonal antibodies, the present inventors prepared an immunocomplex of bi-specific hybrid monoclonal antibody and thrombolytic substance in a ratio of 1 to 1, substantially free of degradation of their antibody activity and thrombolytic activity, by immunologically coupling a thrombolytic substance to the bi-specific hybrid monoclonal antibody, thus developing a fibrin-specific thrombolytic agent. Accordingly, the present invention provides a hybrid MoAb whose two specificities are respectively against fibrin and thrombolytic substance and a polydoma which produces this antibody. Although the present invention is illustrated by use of bi-specific antibodies having specificities against fibrin and a thrombolytic agent, it is not so limited. For example, tri-specific antibodies could be used in the practice of the present invention so long as the speciities against fibrin and thrombolytic agent are retained.

The present invention also provides a thrombolytic agent comprising the above-mentioned hybrid monoclonal antibody and a thrombolytic substance which is immunologically coupled thereto.

Any anti-fibrin-antibody-producing hybridoma can be used for the present invention, as long as it produces a fibrin-specific MoAb which does not substantially bind to fibrinogen. For example, such a fibrin-specific antibody is prepared by the use of an α-chain N-terminal fragment peptide or β-chain N-terminal fragment peptide of the fibrin resulting from fibrinolysis as immunogen [K. Y. Hui et al.: Science, 222, 1129 (1983) or Japanese unexamined Patent Publication No. 93800/1988]. Although any fibrin is acceptable, as long as it is of animal derivation, human fibrin is preferred; it is especially preferable to use a peptide corresponding to the β-chain N-terminal portion of human fibrin. The fibrin-specific antibody thus obtained is coupled with carrier protein, followed by immunization of an animal (e.g. rabbit, rat, mouse, guinea pig) to obtain antibody-producing cells. Antibody-producing cells such as splenocytes or lymph node cells are then collected from the immunized animal and fused with myeloma cells. The hybridoma cells thus obtained are subjected to screening for antibody-producing cells which do not substantially react on fibrinogen and which specifically bind to fibrin. It is preferable that the human fibrin β-chain N-terminal peptide have the following amino acid sequence:

H-Gly-His-Arg-Pro-Leu-Asp-Lys-R-Cys-OH wherein R represents a peptide represented by Lys-Arg-Glu-Glu or a fragment thereof. The C-terminal Cys is used for the linker portion for chemical binding with carrier protein. Accordingly, it is possible to chemically bind the peptide to carrier protein via the SH group of the C-terminal Cys of the peptide by previously maleimidating the carrier protein with N-(γ-maleimidobutyryloxysuccinimide) (hereinafter also abbreviated GMBS) or dithiopyridylating the carrier protein with N-succinimidyl-3-(2pyridyldithio)propionate (hereinafter also abbreviated SPDP).

Any thrombolytic substance can be used for the present invention, as long as it is a protein capable of thrombolysis or a substance which promotes thrombolysis. Examples of such substances include protease or precursors thereof and thrombolysis promoters (e.g. TPA, UK, ProUK, SK, trypsin, plasmin, protein C, protein S). It is preferable to use protease; TPA, UK and derivatives thereof are especially preferable. It does not matter whether the TPA is single- or two-chain. As for UK, single- or two-chain low molecular weight UK, proUK or derivatives of UK [E. Haber et al.: Science, 243,51 (1989)] may be used. For preparing antibody-producing hybridomas, the method is available in which an animal is immunized with the above-mentioned protein in accordance with a standard method and the resulting antibody-producing cells are fused with myeloma cells or other cells. Especially, as the method of producing antibody producing-hybridomas, it is preferable to use antibody producing-cells obtained by immunizing animals with low molecular weight UK. The same procedure as the method of producing anti-fibrin-antibody-producing hybridomas by animal immunization followed by fusion of the resulting antibody-producing cells with myeloma cells or other cells may be used in obtaining hybridomas which produce an antibody against thrombolytic substances.

Examples of animals used for immunization include rabbits, rats, mice and guinea pigs. It is especially preferable to use mice in the case of MoAb production. Inoculation can be achieved in accordance with an ordinary method; for example, 1 to 100 μg, preferably 10 to 25 μg of immunogen protein, in emulsion in equal amounts (0.1 ml) of physiological saline and Freund's complete adjuvant, is subcutaneously or intraperitoneally inoculated at the back or abdomen 3 to 6 times at intervals of 2 to 3 weeks.

From these immunized animals, e.g. mice, are selected individuals with high antibody titer; spleens and/or lymph nodes are collected at 3 to 5 days following the final immunization; antibody-producing cells contained in them are fused with myeloma cells. This fusion can be achieved in accordance with the procedure of a known method. Examples of the fusogen include polyethylene glycol (hereinafter also abbreviated PEG) and Sendai virus. It is preferable to use PEG. Examples of myeloma cell lines which can be used include NS-1, P3U1 and SP2/0; it is preferable to use P3U1. The ratio of e.g. splenocytes and myeloma cells is preferably 1 to 10 of the former to 1 of the latter. It is recommended that PEG with a molecular weight of 1,000 to 6,000 be added to the mixture to reach a concentration of 10 to 80% and incubation be conducted at 20 to 37° C., preferably 30 to 37° C. for 3 to 10 minutes.

Various methods can be used for the screening of anti-fibrin-antibody-producing hybridomas. For example, after fibrinogen adsorption onto a microplate, the fibrinogen is converted to fibrin by the action of thrombin. Then, a hybridoma culture supernatant is added to the fibrin-immobilized microplate in the presence of excess fibrinogen, followed by determination of antibody titer in the culture supernatant by enzyme immunoassay (hereinafter also abbreviated EIA) for plate-bound anti-fibrin specific antibody. The hybridomas found positive for antibody titer are selected and bred using a medium supplemented with HAT (hypoxantine-aminopterin-thymidine) and immediately subjected to cloning, which is normally easily achieved by limited dilution analysis. The desired monoclonal anti-fibrin-specific-antibody-producing hybridoma can be obtained by determining the antibody titer of the cloned hybridoma culture supernatant by the above method and selecting a hybridoma which stably produces an antibody with high titer.

Examples of the anti-fibrin-antibody-producing hybridoma prepared in accordance with the above production method include FIB 1-11 and FIB 2-11, both described in Example 1 given below.

Screening of hybridomas which produce an antibody against thrombolytic substance can easily be achieved by EIA using a microplate onto which the thrombolytic substance has been adsorbed. Cloning can be conducted in accordance with the standard method described above to obtain the desired antibody-producing hybridoma.

Examples of the anti-TPA-antibody-producing hybridoma prepared in accordance with the above production method include TPA 1-41, TPA 1-70, and TPA 2-14 described in Example 2 given below. Examples of the anti-LTK-antibody-producing hybridoma include UK 1-3, UK 1-87, both described in Example 3 given below, and UK 1-6, described in Example 12.

Some methods are available for preparation of a polydoma which produces the hybrid MoAb [e.g. Hiroshi Aramoto et al.: Protein, Nucleic Acid and Enzyme, 33,217 (1988)]. Although any one of these methods can be used to prepare a polydoma which produces a hybrid MoAb for use in the present invention, mention may be made of ① ( the method in which the above HAT-resistant hybridoma which produces an antibody against thrombolytic substance is acclimatized step by step to a culture medium supplemented with 5-bromodeoxyuridine (hereinafter also abbreviated BrdU), followed by cloning of thymidine kinase deficient strain to make it sensitive to HAT; similarly, an HAT-resistant anti-fibrin-specific-antibody-producing hybridoma is made resistant to 8-azaguanine (hereinafter also abbreviated AZG), followed by cloning of a hypoxanthine-guanine-phosphoribosyl transferase deficient strain to make it sensitive to HAT; the tetraomas obtained by fusing these two cloned hybridomas in accordance with methods known to those skilled in the art are subjected to screening using an HAT-supplemented medium for a tetraoma which secretes a hybrid MoAb capable of binding to both fibrin and thrombolytic substance, which is then cloned; and ② the method in which an anti-fibrin-specific-antibody-producing hybridoma is labeled with fluorescein isothiocyanate (hereinafter abbreviated FITC) and another hybridoma which produces an antibody against thrombolytic substance is labeled with tetramethyl rhodamine isothiocyanate (hereinafter also abbreviated TRITC), followed by fusion of these two hybridomas in accordance with methods known to those skilled in the art; the obtained cell suspension is applied to a fluorescein activated cell sorter (hereinafter also abbreviated FACS) to select and clone the tetraoma having both the green fluorescence of FITC and red fluorescence of TRITC. It is also possible to use the markers of both parent strains in reverse to select and clone the tetraoma.

In cell fusion using these procedures, a fusogen such as Sendai virus or PEG, electric stimulation or other means can be used. It is preferable to use PEG. An example is given below, but this is not to be construed as limitative. PEG with a degree of polymerization of about 1,000 to 6,000 is normally used at a concentration of about 10 to 80% for a treatment time of about 0.5 to 30 minutes. Efficient fusion can be achieved under preferable conditions, for example, by keeping about 35 to 55% PEG 6,000 in contact with cells at 37° C. for about 4 to 10 minutes.

Polydoma selection can be achieved using the above-mentioned HAT-supplemented medium. For this purpose, chemical acclimatization is conducted using 8-AZG, 6-thioguanine (6-TG) or 5-BrdU to obtain strains resistant to respective chemicals. Various selection media can be used by introducing a new marker into fused cells. Examples of such selection media include neomycin-supplemented medium and hygromycin B-supplemented medium [B. Sugden et al.: Molecular and Cellular Biology, 5, 410 (1985)].

Another method is also available in which two hybridomas labeled with different fluorescent dyes are fused together, followed by sorting a double-labeled hybrid hybridoma using FACS [L. Karawajew et al.: Journal of Immunological Methods, 96, 265 (1987)].

Various methods can be used for screening of hybrid antibody-producing polydomas. For example, it is possible to use in appropriate combination the following methods or their modifications: ① combination of the above-mentioned EIA procedures respectively for screening of anti-fibrin-specific-antibody-producing hybridomas and for screening of hybridomas which produce an antibody against thrombolytic substance, ② EIA for detection of bi-specific hybrid antibody by adding the subject culture supernatant to a fibrin-coupled microplate and then adding an HRP-labeled thrombolytic substance, and, when using an antibody against a thrombolytic substance belonging to a subclass different from that of the anti-fibrin specific antibody, ③ EIA for detection of a hybrid antibody by adding the subject culture supernatant to a fibrin-coupled microplate and then adding the HRP-labeled anti-mouse-IgG-subclass specific antibody.

The polydomas found positive for hybrid antibody activity are immediately subjected to cloning, which is typically achieved by limiting dilution analysis. The desired monoclonal hybrid antibody-producing polydoma can be obtained by determining the antibody titer of the cloned polydoma culture supernatant by the above method and selecting a polydoma which stably produces an antibody with high titer.

The above-mentioned polydoma of the present invention can typically be cultivated in liquid medium or in the peritoneal cavity of animals (e.g. mammals such as mice) by a known method. Known biochemical techniques can be used in combination to purify the antibody in the culture broth and ascites fluid. For example, the cell culture broth or ascites fluid is centrifuged; the resulting supernatant is taken and subjected to salting-out (normally using ammonium sulfate or sodium sulfate). The resulting protein precipitate is dissolved in an appropriate solution and dialyzed, followed by column chromatography (ion exchange column, gel filtration column, protein A column, hydroxyapatite column etc.) to separate and purify the desired antibody. This separation purification procedure gives about 1 to 5 mg of bi-specific hybrid MoAb with a purity of over 80% in a ratio by protein weight from 1 l of culture supernatant, for instance. The same antibody can be obtained with a yield of 3 to 10 mg from 20 ml of ascites fluid.

The bi-specific hybrid MoAb thus obtained is a homogeneous protein; its treatment with protease (e.g. pepsine) etc. gives F(ab')2 or other fragment capable of binding to both fibrin and thrombolytic substance.

Examples of the bi-specific hybrid antibody-producing polydoma prepared in accordance with the above production method include the tetraomas described in Examples 4,5 and 13 given below.

In addition to the tetraomas formed between an anti-fibrin-MoAb-producing hybridoma and another hybridoma which produces an antibody against thrombolytic substance, mentioned above as examples of the polydoma which produces the hybrid MoAb of the present invention, there can be used triomas formed between a hybridoma which produces one MoAb and a cell which produces another MoAb, hybridomas obtained by fusing cells which produce respective MoAb after being immortalized with Epstein-Barr virus, and other hybridomas, for the same purpose, as long as they produce the hybrid MoAb of the present invention.

When these polydomas produce mouse IgG MoAb, it is possible to prepare a mouse-human chimeric antibody by obtaining a DNA which encodes a variable or hyper-variable region containing the antigen recognition site for this bispecific hybrid MoAb and then binding a gene which encodes the constant region of human IgG to this DNA using a gene manipulation technique [Z. Steplewski et al.: Proceedings of the National Academy of Science, USA, 85, 4852 (1988)]. This chimeric antibody is preferably used because of its low antigenicity in administration to humans.

Some methods are available for thrombolytic therapy using the hybrid MoAb of the present invention or a selective thrombolytic protein complex prepared from a thrombolytic substance and the hybrid MoAb, including ① the method in which the hybrid MoAb of the present invention is previously administered to the thrombotic disease patient and a thrombolytic substance such as TPA or UK is administered after elapse of sufficient time to allow it to bind to the thrombi formed in the patient's body, ② the method in which the hybrid MoAb and a thrombolytic substance are administered to the thrombotic disease patient at the same time, and ③ the method in which the hybrid MoAb and a thrombolytic substance are previously reacted and, after separation of the unreacted portion of the thrombolytic Substance, the obtained selective thrombolytic protein complex is administered to the thrombotic disease patient.

The thrombolytic agent, hybrid MoAb or thrombolytic substance of the present invention can be prepared as injection directly or in mixture with appropriate pharmacologically acceptable carrier, excipient or diluent after germ removal by filtration through membrane filter as necessary, and administered to mammals (e.g. mice, rats, cats, dogs, swine, bovines, monkeys, humans) for the purpose of treatment of thrombotic or obstructive diseases such as myocardial infarction, peripheral arteriovenous obstruction, retinal arteriovenous obstruction, cerebral infarction and pulmonary embolism.

Although depending upon the type of the target disease, its symptom and route of administration, the daily dose of the thrombolytic agent of the present invention, in intravenous administration to adult myocardial infarction patients, for instance, is typically about 0.02 to 1 mg/kg, preferably about 0.04 to 0.4 mg/kg as hybrid MoAb, and, for thrombolytic substances, about 0.01 to 0.5 mg/kg, preferably about 0.02 to 0.2 mg/kg as TPA and about 0.01 to 0.5 mg/kg, preferably about 0.02 to 0.2 mg/kg as UK.

The hybrid MoAb of the present invention is capable of specifically binding to fibrin while it does not substantially react on fibrinogen and specifically binding to a thrombolytic substance without spoiling its capability of fibrinolysis. It is therefore possible to easily prepare a 1:1 immunocomplex of the hybrid MoAb and a thrombolytic substance; their use in combination permits selective and efficient lysis or removal of thrombi.

The method described above permits selective and efficient lysis and removal of thrombi by the use of the hybrid MoAb of the present invention, which is capable of specifically binding to the target thrombus site and which does not substantially bind with fibrinogen, in combination with a thrombolytic substance.

EXAMPLES

The present invention is hereinafter described in more detail by means of the following reference examples and working examples; these examples are not to be construed as limitative on the scope of the present invention.

The animal cell lines used in Examples have been deposited with the Institute of Fermentation, 17-85, Juso-honomachi 2-chome, Yodogawa-ku, Osaka 532, Japan and Fermentation Research Institute, Ministry of International Trade and Industry, 1-3, Higashi 1-chome, Tukuba-shi, Ibaraki-ken 305, Japan, under accession numbers listed in the table below. FIE 1-11, FIB 2-11, TPA 1-41, TPA 1-70, UK 1-3 and UK 1-87 were deposited on Oct. 4, 1988; FT2-14 was deposited on Nov. 25, 1988; FU1-74 was deposited on Mar. 14, 1989; TPA 2-14 was deposited on Jul. 18, 1989; UK 1-6 and FU 2-16 were deposited on Aug. 11, 1989.

| Animal cell line | (IFO) IFO No. | (FRI) FERM No. |
| --- | --- | --- |
| Mouse hybridoma FIB 1-11 | 50174 | BP-2081 |
| Mouse hybridoma FIB 2-11 | 50175 | BP-2082 |
| Mouse hybridoma TPA 1-41 | 50178 | BP-2085 |
| Mouse hybridoma TPA 1-70 | 50179 | BP-2086 |
| Mouse hybridoma TPA 2-14 | 50194 | BP-2519 |
| Mouse hybridoma UK 1-3 | 50176 | BP-2083 |
| Mouse hybridoma UK 1-87 | 50177 | BP-2084 |
| Mouse hybridoma UK 1-6 | 50208 | BP-2548 |
| Mouse hybrid-hybridoma (tetraoma) FT2-14 | 50180 | BP-2158 |
| Mouse hybrid-hybridoma (tetraoma) FU1-74 | 50185 | BP-2334 |
| Mouse hybrid-hybridoma (tetraoma) FU 2-16 | 50207 | BP-2547 |

IFO: Institute for Fermentation, Osaka
FRI: Fermentation Research Institute, Ministry of International Trade and Industry In the present specification, amino acids and peptides are represented by abbreviations based on the abbreviation system adopted by the IUPACIUB Commission on Biochemical Nomenclature (CBN); example abbreviations are given below. Note that when there is a possibility of the existence of an optical isomer in particular amino acid etc., it is an L-amino acid unless otherwise stated.

Gln: Glutamine residue

Asp: Aspartic acid residue

Pro: Proline residue

Tyr: Tyrosine residue

Val: Valine residue

Lys: Lysine residue

Glu: Glutamic acid residue

Ala: Alanine residue

Ash: Asparagine residue

Leu: Leucine residue

Phe: Phenylalanine residue

Gly: Glycine residue

His: Histidine residue

Ser: Serine residue

Thr: Threonine residue

Ile: Isoleucine residue

Trp: Tryptophan residue

Arg: Arginine residue

Met: Methionine residue

Cys: Cysteine residue

Reference Example 1

(EIA for anti-fibrin antibody measurement)

To a 96-well microplate was dispensed a 1 mg/ml human fibrin monomer solution in a 20 mM phosphate buffer solution (PBS, pH 7.3) containing 3.3 M urea and 0.01% EDTA at 50 µl per well. After leaving this microplate at 4° C. overnight, 150 µl of PBS containing 2% casein and 0.01% thimerosal was added to prepare a sensitized plate. Then, a 10 mg/ml human fibrinogen solution in PBS containing 100 unit/ml heparin and 3 mM phenylmethylsulfonyl fluoride was mixed with an equal amount of the subject hybridoma culture supernatant. After reaction at room temperature for 30 minutes, 100 µl of the mixture was added to the above fibrin-sensitized plate, followed by reaction at room temperature for 2 hours. After thoroughly washing the plate with PBS containing 0.05% Tween 20 (PBS-TW), a horseradish peroxidase (HRP) labeled rabbit anti-mouse-IgG antibody was added, followed by reaction at room temperature for 2 hours.

After plate washing, a 0.1 M citrate buffer solution containing orthophenylenediamine and $H_2O_2$ as enzyme substrates was added to each well, followed by enzyme reaction at room temperature. After termination of the reaction by the addition of 1 N sulfuric acid, the coloring pigment was quantitated at a wavelength of 492 nm using the Multiscan (produced by Flow Co.).

Reference Example 2

(EIA for measuring anti-TPA antibody)

A 5 µg/ml TPA solution was dispensed to a 96-well microplate at 100 µl per well and left at 4° C. overnight, followed by addition of 150 µl of PBS containing 2% casein and 0.01% thimerosal to prepare a sensitized plate. After removing the above solution and washing the plate with PBS-TW, 100 µl of the subject hybridoma culture supernatant was added, followed by reaction at room temperature for 2 hours. Thereafter, enzyme reaction was carried out by the method of Reference Example 1 and antibody titer was determined.

Reference Example 3

(EIA for measuring anti-UK antibody)

After a UK-sensitized plate was prepared in the same manner as in Reference Example 2 but UK was used in place of TPA, anti-UK antibody titer was determined in the same manner.

Reference Example 4

(EIA for measuring anti-fibrin-anti-TPA hybrid antibody ①) To a fibrin-sensitized plate as prepared in Reference Example 1 was added the subject hybridoma culture supernatant, followed by reaction at room temperature for 2 hours. After plate washing with PBS-T, biotin-labeled TPA was added, followed by reaction at room temperature for 2 hours. An avidin-HRP complex was then added, followed by reaction at room temperature for 1 hour; the activity of HRP bound to the solid phase was determined by the method of Reference Example 1.

Reference Example 5

(EIA for measuring anti-fibrin-anti-UK hybrid antibody ①)

The procedure of Reference Example 4 was followed but biotin-labeled UK was used in place of biotin-labeled TPA. Thereafter, anti-fibrin-anti-UK hybrid antibody titer was determined in the same manner.

Reference Example 6

(Fibrinolysis neutralization test)

To a TPA solution (final concentration 20 ng/ml) or UK solution (final concentration 25 ng/ml) was added a dilution of the subject hybridoma culture supernatant, followed by reaction at 37° C. for 1 hour. The reaction mixture was then dispensed to a fibrin-agarose plate at 5 µl per well, followed by incubation at 37° C. for 2 to 6 hours. The diameter of the resulting fibrinolysis plaque was measured to determine the ability of the MoAb in the hybridoma culture supernatant to neutralize the enzyme activity of TPA or UK.

Reference Example 7

(EIA for measuring anti-fibrin-anti-TPA hybrid antibody②)

To a TPA sensitized plate as prepared in Reference Example 2 was added the subject solution containing the hybrid antibody, followed by reaction at room temperature for 2 hours. After plate washing with PBS-TW, an HRP-labeled anti-mouse-$IgG_1$ ($\gamma_1$-chain specific) antibody (commercially available from Cosmo-Bio K.K.) was added, followed by reaction at room temperature for 2 hours. After thoroughly washing the plate with PBS-TW, the activity of HRP bound to the solid phase was determined by the method of Reference Example 1.

Reference Example 8

(EIA for measuring anti-fibrin-anti-TPA hybrid antibody ③)

To a TPA-sensitized plate as prepared in Reference Example 2 was added the subject solution containing the hybrid antibody, followed by reaction at room temperature for 2 hours. After plate washing with PBS-TW, the human fibrin β-chain N-terminal peptide (1-11)-BSA complex described in Example 1-①, labeled with biotin, was added, followed by reaction at room temperature for 2 hours. An avidin-HRP complex was then added, followed by reaction at room temperature for i hour; the activity of HRP bound to the solid phase was determined by the method of Reference Example 1.

Reference Example 9

(EIA for measuring anti-fibrin-anti-UK hybrid antibody ②)

To a UK-sensitized plate as prepared in Reference Example 3 was added the subject solution containing the hybrid antibody, followed by reaction at room temperature for 2 hours. After plate washing with PBS-TW, the human fibrin β-chain N-terminal peptide (1-11)-BSA complex described in Example 1-①, labeled with biotin, was added, followed by reaction at room temperature for 2 hours. An avidin-HRP complex was then added, followed by reaction at room temperature for 1 hour; the activity of HRP bound to the solid phase was determined by the method of Reference Example 1.

Reference Example 10

(EIA for determination of anti-low-molecular-weight,UK antibody titer)

After preparation of a plate sensitized with low molecular weight UK (two-chain low molecular weight UK, available from JCR Co.) in place of the TPA described in Reference Example 2, anti-low-molecular-weight-UK antibody titer was determined in the same manner.

Reference Example 11

(UK enzyme activity neutralization test)

To a UK solution (final concentration 1.7 μg/ml) was added a subject antibody solution, and reaction was carried out at room temperature for 30 minutes. To the reaction mixture was added synthetic peptide substrate S-2444 (1 mM, pyroglutamyl glycyl arginyl paranitroanilide, produced by Kabi Co.). After reaction at 37° C. for 15 minutes, liberated paranitroanilide (absorbance at 405 nm) was measured.

Example 1

(Preparation: of hybridomas which produce mouse anti-human-fibrin monoclonal antibody)

① Preparation of immunogen

To an aqueous solution of 12 mg/2ml bovine serum albumin (BSA), previously maleimidated with GMBS (maleimido groups were introduced at 13 mols per mol BSA), was added 3.3 mg of a human fibrin β-chain N-terminal peptide (1-11)-Cys prepared by the known solid phase synthesis method using a peptide synthesizer (Model 430A, Applied System Co.), followed by reaction at 30° C. for 1 hour to yield a human fibrin 13-chain N-terminal peptide (1-11)-BSA complex. After 3 times of dialysis with physiological saline solution (3 l×3), this complex was stored under freezing conditions and then used as immunogen.

② Immunization

To a 1 mg/ml peptide-BSA complex solution in physiological saline solution was added an equal amount of Freund's complete adjuvant, followed by subcutaneous immunization of mice (♀,n=10:0.1 mg/0.2 ml/mouse) at the back and abdomen. Additional immunization was conducted by inoculating the immunogen in combination with an equal mount of Freund's incomplete adjuvant 5 times at intervals of 2 to 3 weeks.

③ Cell fusion

At 3 days following the final immunization, spleens were excised and a splenocyte suspension was prepared by a standard method [S.M. North et al.: Immunology, 47,397(1982)] (about $10^8$ cells). After addition of $2\times10^7$ mouse myeloma cells (P3U1), cell fusion was conducted in accordance with the method of Köhler and Milsrein [Nature, 256,495 (1975)] using PEG 6000.

After completion of the fusion, the cell mixture was suspended in HAT medium, which contains hypoxanthine, aminopterin and thymidine, followed by cultivation for 10 days. Immediately after completion of the selection of parent cells, the HAT medium was replaced with HT medium, which lacks aminopterin, followed by further cultivation. ④ Selection and cloning of hybridomas The antibody titer of the hybridoma culture supernatant was determined by the EIA procedure described in Reference Example 1, which uses a human fibrin monomer adsorbed microplate as the solid phase. At 10 to 20 days following the fusion, hybridomas appeared and an antibody which specifically bound to human fibrin was detected. The .hybridomas found to have especially strong avidity were subjected to cloning by limiting dilution method.

The culture supernatant of cloned hybridomas was subjected to screening by EIA; hybridomas with strong avidity to human fibrin were selected.

As a result, mouse hybridomas FIB 1-11 and FIB 2-11 were obtained, both of which produce an MoAb which specifically binds to fibrin in the presence of high concentrations of fibrinogen. Antibodies FIB 1-11 and FIB 2-11 respectively produced by these two hybridomas were both identified as $IgG_1$ in immunoglobulin class and subclass by the Ouchterlony method.

These anti-human-fibrin specific antibodies FIB 1-11 and FIB 2-11 were measured in the presence and absence of fibrinogen by the EIA procedure described in Reference Example 1. The results are shown in Table 1. Note that anti-human-fibrinogen antibody FIB 2-162 obtained by the procedure described in Example 1 was used as control.

TABLE 1

| | EIA for Measuring Anti-fibrin Antibody[1] | |
|---|---|---|
| | Optical absorbance (492 nm) | |
| Monoclonal antibody | In the absence of fibrinogen | In the presence of fibrinogen[2] |
| FIB 1-11 | 0.50 | 0.20 |
| FIB 2-11 | 0.51 | 0.16 |
| FIB 2-162 | 0.32 | 0.01 |

[1] EIA described in Reference Example 1.
[2] Final concentration 5 mg/ml.

Example 2

(Preparation of hybridomas which produce mouse anti-TpA monoclonal antibody)

① Immunization

To a solution of 200 μg/ml of a commercially available single-chain TPA (available from Chuo Kagaku Kogyo K.K.) in physiological saline solution was added an equal mount of Freund's adjuvant. This emulsion was subcutaneously administered to BALB/c mice (♀, 20 μg/0.2 ml/mouse) at the back and abdomen, followed by additional immunization at intervals of 2 to 3 weeks. A TPA antigen solution (50 μg/0.1 ml physiological saline solution/mouse) was intravenously administered to animals which had the maximum serum antibody titer at 10 days following the 3 times of additional immunization.

② Cell fusion

Cell fusion was conducted in accordance with the method described in Example 1-③.

③ Selection and cloning of hybridomas

Hybridomas were screened by the EIA procedure described in Reference Example 2, which uses a TPA-bound microplate. Thereafter, the procedure of Example 1-④ was followed to obtain anti-TPA-MoAb-producing hybridomas. Out of these hybridomas were obtained a mouse hybridoma TPA 1-41, which produces an anti-TPA MoAb, which specifically binds to TPA without spoiling the capability of fibrinolysis, a mouse hybridoma TPA 1-70, which produces a TPA neutralizing antibody and a mouse hybridoma TPA 2-14, which produces a TPA non-neutralizing antibody which competitively binds to TPA with plasminogen activator inhibitor (PAD. Antibodies TPA 1-41, TPA 1-70 and TPA 2-14 respectively produced by these three hybridomas were respectively identified as $IgG_2b$, $IgG_1$ and $IgG_1$ in immunoglobulin class and subclass by the Ouchterlony method.

Figure 1:
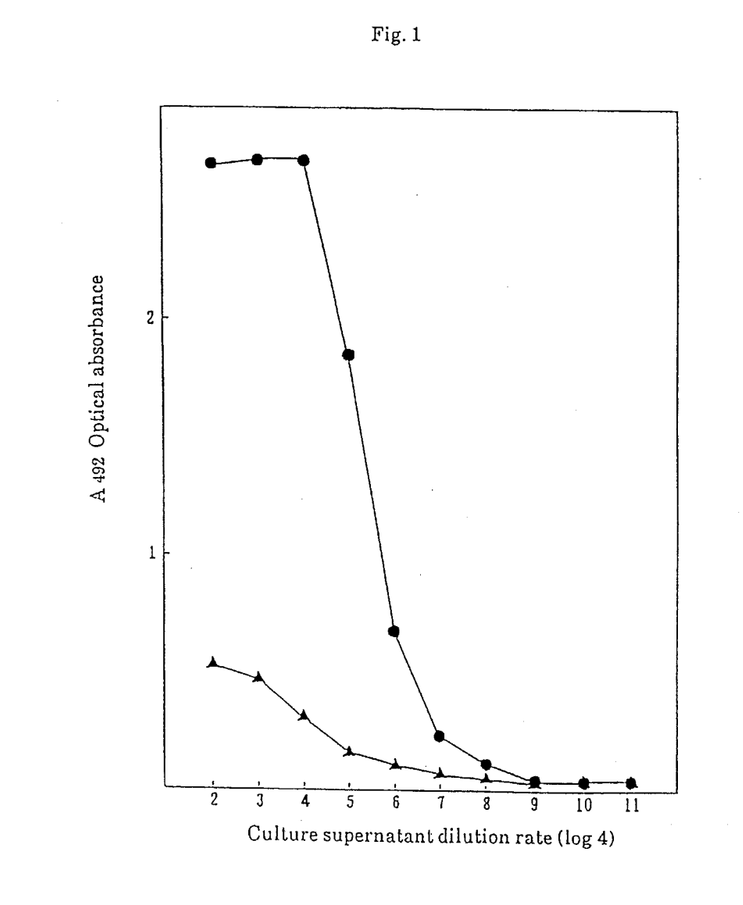
FIG. 1 shows the dilution curve of the anti-TPA specific antibodies TPA 1-41 and TPA 1-70 prepared by the EIA procedure described in Reference Example 2 (see Example 2).

FIG. 1 shows the results of measurement of these anti-TPA specific antibodies TPA 1-41 (—●—) and TPA 1-70 (—▲—) by the EIA procedure described in Reference Example 2.

Example 3

(Preparation of hybridomas which produce mouse anti-UK monoclonal antibody)

① Immunization

Mouse immunization was conducted in exactly the same manner as in Example 2-① but UK (produced by Nihon Seiyaku) was used in place of TPA described in Example 2-①.

② Cell fusion

Cell fusion was conducted in accordance with the method described in Example 1-③.

③ Selection and cloning of hybridomas

Hybridomas were screened by the EIA procedure described in Reference Example 3, which uses a UK-bound microplate. Thereafter the procedure of Example 1-④ was followed to obtain anti-UK-MoAb-producing hybridomas. Out of these hybridomas were obtained mouse hybridomas UK 1-3 and UK 1-87, both of which produce an anti-UK MoAb, which specifically binds to UK without spoiling its capability of fibrinolysis. Antibodies UK 1-3 and UK 1-87 respectively produced by these two hybridomas were respectively identified as IgG$_1$ and IgG$_2$b in immunoglobulin class and subclass by the Ouchterlony method.

Figure 2:
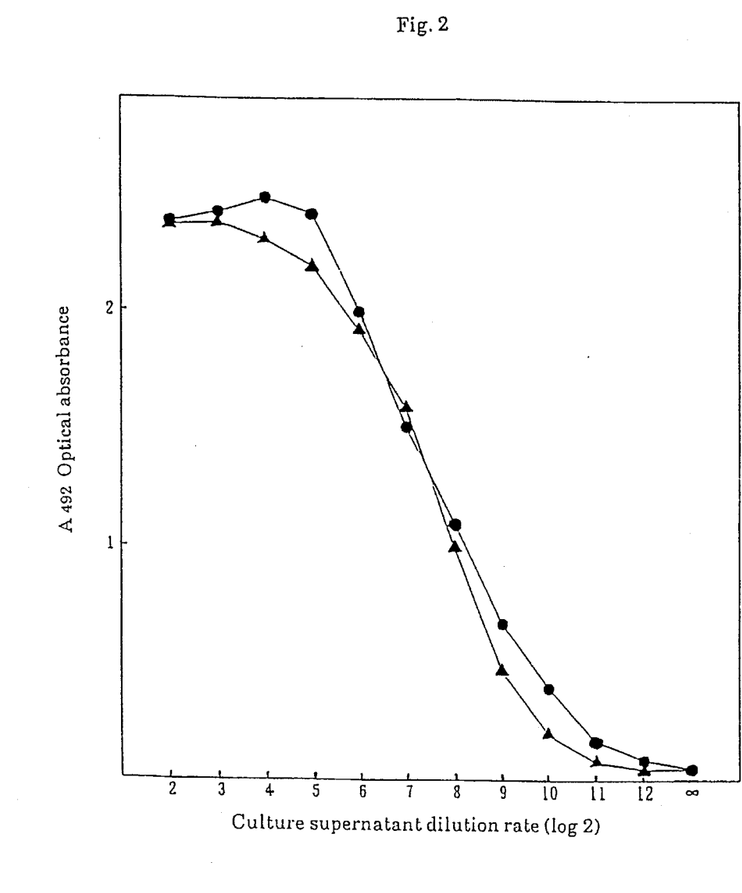
FIG. 2 shows the dilution curve of the anti-UK specific antibodies UK 1-3 and UK 1-87 prepared by the EIA procedure described in Reference Example 3 (see Example 3).

FIG. 2 shows the results of measurement of these anti-UK specific antibodies UK 1-3 (—●—) and UK 1-87 (—▲—) by the EIA procedure described in Reference Example 3.

Example 4

(Production of hybrid monoclonal antibody possessing anti-TPA-anti-human-fibrin bi-specificity)

① Cell fusion

The hybridoma FIB 1-11 obtained in Example 1, which produces anti-human-fibrin antibody, and the hybridoma TPA 1-41 obtained in Example 2, which produces anti-TPA antibody, were each incubated in an Iscove-Ham F-12 medium containing 0.5 μg/ml FITC and 1.5 μg/ml TRrrC at 37° C. for 30 minutes for fluorescent staining. An LSM solution (commercially available from Wako Pure Chemical Industries Ltd.) was then added and the dead cells were removed. These two hybridomas were then mixed together at a ratio of 1 to 1, followed by cell fusion by the method described in Example 1-③ using PEG 6000.

After incubation at 37° C. for 2 hours, the cell mixture was applied to FACS, whereby 25,000 fluorescein-rhodamine double stained cells. These double stained cells were seeded and cultivated on a 96-well microplate at 10 cells per well, the microplate previously seeded with mouse thymocytes at 5×105 cells/well as feeder cells.

② Selection and cloning of hybrid hybridomas

The culture supernatants from wells in which cell proliferation occurred in 1 to 2 weeks after fusion were each subjected to the EIA procedures described in Reference Examples 1, 2, 7 and 8 to determine antibody activity. The antibody activity of culture supernatants of the hybridomas FIB 1-11 and TPA 1-41 respectively obtained in Examples 1-④ and ②-3, as controls, was determined in the same manner. The results are shown in Table 2.

The wells which exhibited high hybrid antibody titer were subjected to cloning by limiting dilution method; the desired bi-specific-antibody-producing mouse hybrid hybridoma (tetraoma) FT 2-14 was obtained.

TABLE 2

Specificity of Antibodies Produced by Hybrid Hybridomas
1): Hybrid hybridoma obtained in Example 4-②.
2): Hybridoma obtained in Example 1-④.
3): Hybridoma obtained in Example 2-③.

| Hybridoma culture supernatant | EIA antibody titer[4] | | | |
|---|---|---|---|---|
| | Anti-fibrin[5] | Anti-TPA[6] | Anti-TPA-anti-mouse-IgG$_1$[7] | Anti-TPA-anti-fibrin β-chain N-terminal peptide[8] |
| Hybrid hybridoma A[1] | 0.66 | 0.99 | 1.90 | 2.45 |
| Hybrid hybridoma B[1] | 0.30 | 0.60 | 0.51 | 2.19 |
| FIB 1-11[2] | 0.29 | 0.00 | 0.01 | 0.00 |
| TPA 1-41[3] | 0.01 | 1.01 | 0.01 | 0.00 |

[4] Expressed in optical absorbence at 492 nm (see Reference Example 1).
[5] EIA described in Reference Example 1.
[6] EIA described in Reference Example 2.
[7] EIA described in Reference Example 7.
[8] EIA described in Reference Example 8.

③ Purification of hybrid antibody

Mouse hybrid hybridoma (tetraoma) FT 2-14 was intraperitoneally inoculated at 5×106 cells/mouse to six BALB/c mice which previously received 0.5 ml of mineral oil by intraperitoneal administration. About 10 to 20 days later, 20 ml of accumulated ascites fluid was collected and subjected to salting-out with 50% saturated ammonium sulfate to yield an IgG fraction. After dialysis against 20 mM PBS (pH 7.5), the IgG fraction was applied to a column of fibrin-coupled Cellulofine and eluted with a 0.2 M glycine-HCl buffer solution of pH 2.9. After dialysis against PBS, the acid elution fraction was applied to a column of TPA-coupled Sepharose 4B and eluted with a 0.2 M glycine-HCl buffer solution of pH 2.3. The eluate was dialyzed against PBS to yield 9.4 mg of bi-specific antibody FT2-14.

Figure 3:
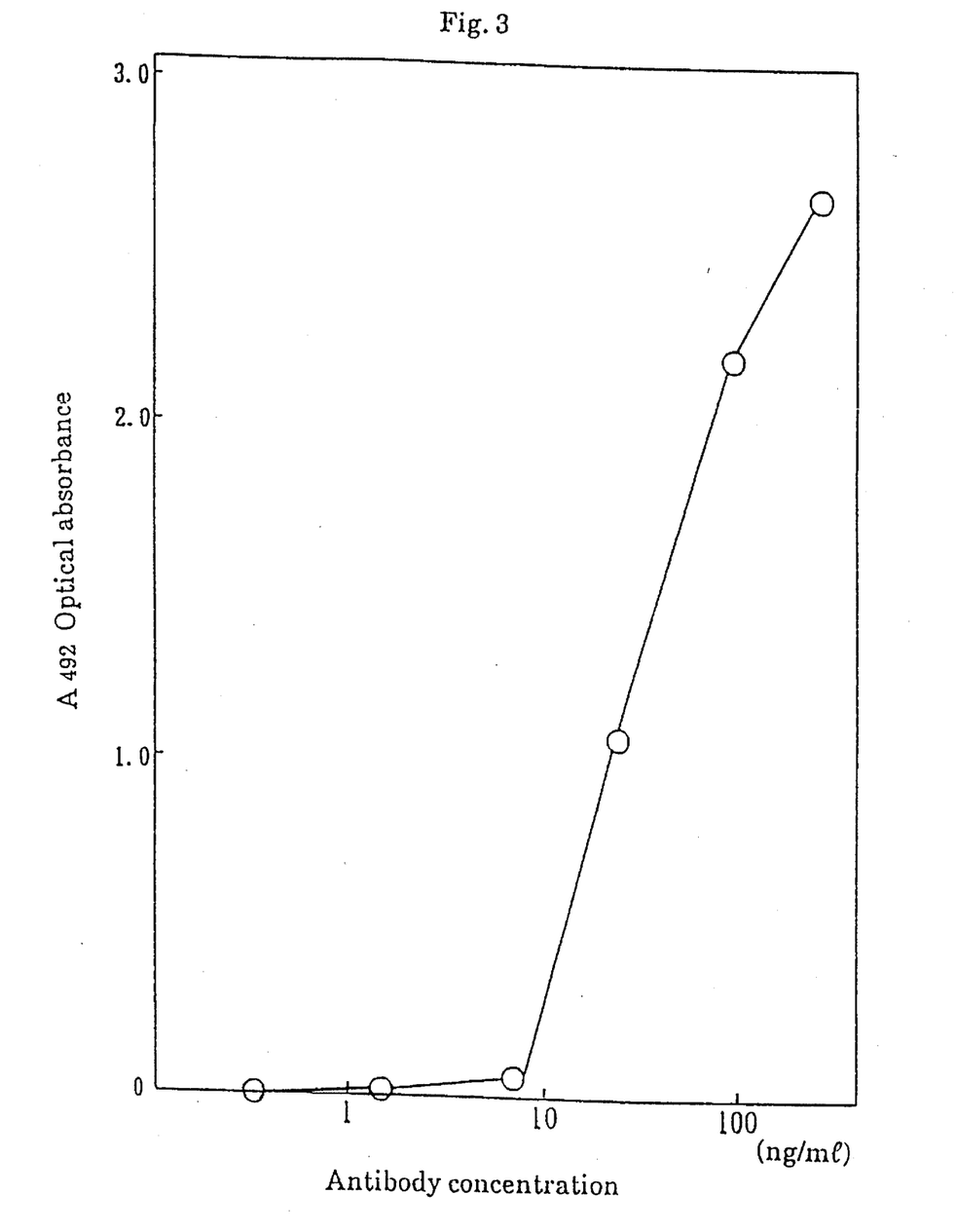
FIG. 3 shows the dilution curve of the anti-TPA-anti-human-fibrin bi-specific antibody FT 2-14 prepared by the EIA procedure described in Reference Example 8 (see Example 4).

The obtained antibody was subjected to the EIA procedure described in Reference Example 8; the dilution curve of the bi-specific antibody was drawn. The results are shown in FIG. 3. From FIG. 3, it is evident that the obtained antibody exhibited strong avidity to both TPA and fibrin.

Example 5.

(Production of hybrid monoclonal antibody possessing anti-UK-anti-human-fibrin bi-specificity①)

① Cell fusion

In accordance with the method described in Example 4-①, the hybridoma FIB 1-11 obtained in Example 1, which produces anti-human-fibrin antibody, and the hybridoma UK 1-3 obtained in Example 3, which produces anti-UK antibody, were each subjected to fluorescent staining with FITC and TRITC, followed by cell fusion using PEG 6000. The cell mixture was applied to FACS; double-stained cells were selected and cultivated.

② Selection and cloning of hybrid hybridomas

The culture supernatants from wells in which cell proliferation occurred at 1 to 2 weeks following the fusion were each subjected to the EIA procedure described in Reference Examples 1, 3 and 9 to determine their antibody activity. The antibody activity of the culture supernatant of the hybridomas FIB 1-11 and UK 1-3 respectively obtained in Examples 1-④ and 3-③, as controls, was determined in the same manner.

The well which exhibited the maximum hybrid antibody activity was subjected to cloning by limiting dilution method to obtain the desired bi-specific-antibody-producing mouse hybridoma FU 1-74.

③ Purification of hybrid antibody

Ascites fluid was collected in accordance with the method described in Example 4-③, followed by salting-out with ammonium sulfate and immunoaffinity chromatography using a fibrin-coupled column and a UK-coupled column; 14 mg of FU 1-74, the anti-UK-anti-human-fibrin bi-specific antibody of the present invention, was obtained from about 20 m4of ascites fluid.

Figure 4:
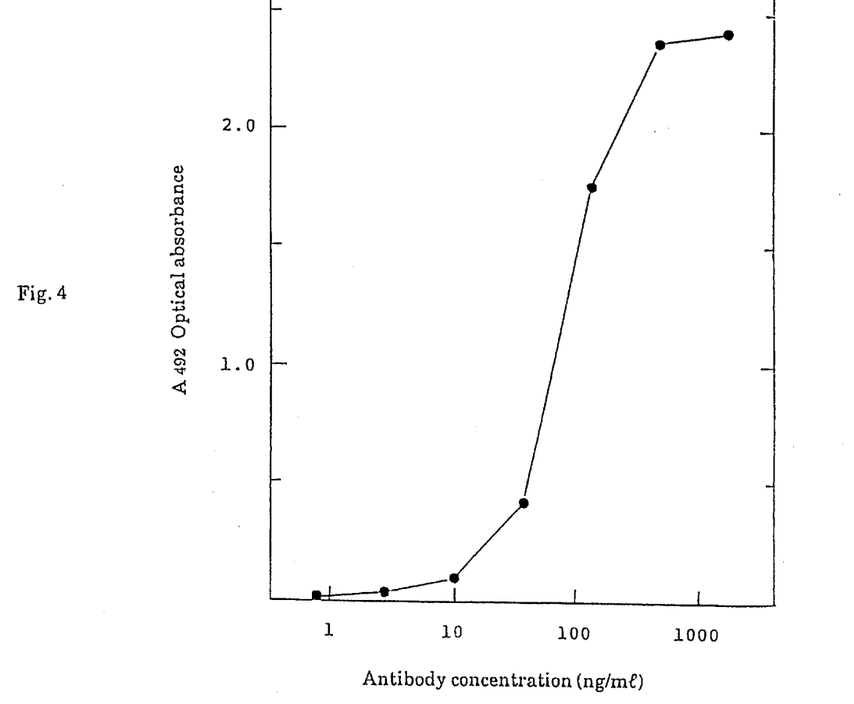
FIG. 4 shows the dilution curve of the anti-UK-anti-human-fibrin bi-specific antibody FU 1-74 prepared by the EIA procedure described in Reference Example 9 (see Example 5).

The obtained antibody was subjected to the EIA procedure described in Reference Example 9; the dilution curve of the bi-specific antibody was drawn. The results are shown in FIG. 4. From FIG. 4, it is evident that the obtained FU 1-74 antibody has strong avidity to both UK and fibrin.

Example 6

(Property① of anti-TPA-anti-human-fibrin bi-specific antibody FT 2-14)

Figure 5:
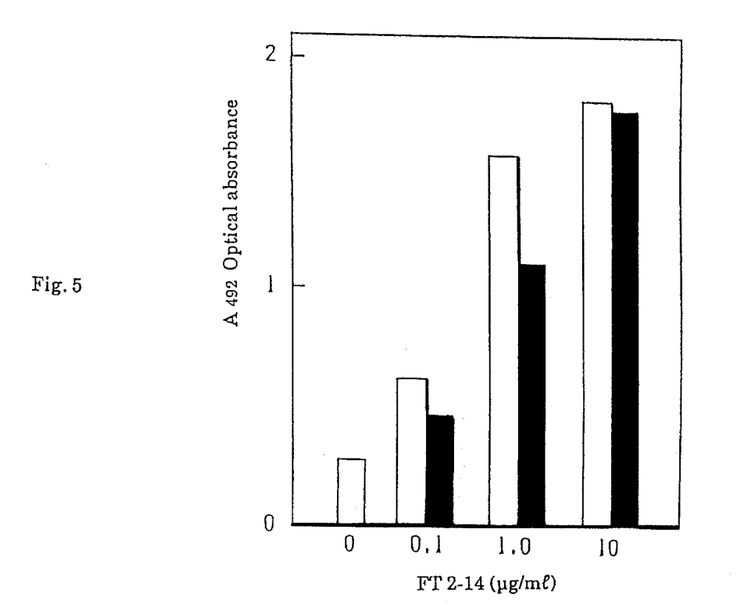

A paper disk of 9.5 mm in diameter was immersed in a 2 ml/me human fibrinogen solution, followed by addition of human thrombin (50 unit/ml) to form a fibrin clot on the paper disk. After thorough washing, this fibrin-coupled paper disk was immersed in a solution of the bi-specific antibody FT 2-14 obtained in Example 4-③ in the presence of fibrinogen (3 mg/ml). The amount of antibody bound to the paper disk was measured using HRP-labeled anti-mouse-IgG$_2$b antibody. The results are shown in FIG. 5.

The fibrin avidity obtained in the presence of fibrinogen (3 mg/ml) (■) was nearly equal to that obtained in the absence thereof (□); it was demonstrated that the FT 2-14 antibody of the present invention is specific to fibrin.

Example 7

(Property② of anti-TPA-anti-human-fibrin bi-specific antibody FT 2-14)

TPA, at various concentrations, was reacted with a solution of the bi-specific antibody FT 2-14 obtained in Example 4-③ of a molar concentration of 4.3 times that of the TPA at 37° C. for 30 minutes to yield an immunocomplex of TPA and FT 2-14 antibody (TPA/FT 2-14 antibody), followed by addition of 3 mM synthetic peptide substrate S-2288 (produced by Kabi Co.) and reaction at 37° C. for 2 hours. The optical absorbance of the liberated para-nitroaniline was determined at 405 nm; the enzyme activity of the above TPA-FT 2-14 antibody complex was compared with that of simple TPA. The results are shown in FIG. 6.

Figure 6:
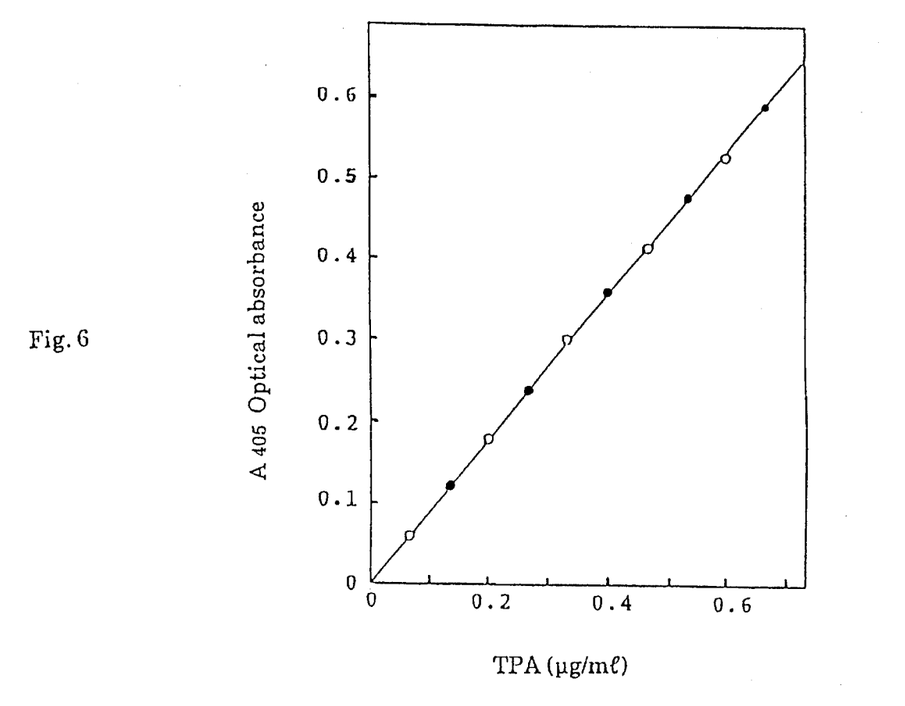
FIG. 6 shows the results of comparison of enzyme activity between the immunocomplex (●) of TPA and the bi-specific antibody FT 2-14 prepared in Example 4-3 and simple TPA (o)(see Example 7).

In FIG. 6, ● shows the enzyme activity of TPA/FT 2-14 antibody complex; ○ shows the enzyme activity of unconjugated TPA. It was demonstrated that TPA does not reduce its enzyme activity at all even when bound with the bi-specific antibody FT 2-14 of the present invention.

Example 8

(Property③ of anti-TPA-anti-human-fibrin bi-specific antibody FT 2-14)

Human fibrinogen was insolubilized by binding it to Cellulofine grains (commercially available from Seikagaku Kogyo K.K.) in accordance with a known method [Etsuko Ebisui et al.: Seikagaku, 54, 732 (1982)], after which it was converted to fibrin by the addition of human thrombin. To 0.2 g of this fibrin-Cellulofine grain complex was added a 10 μg/500 μl of FT 2-14 antibody solution, followed by reaction at 37° C. for 90 minutes. After thorough washing, the reaction mixture was reacted with 100 ng of TPA at 7° C. for 40 minutes. After washing, the reaction mixture was reacted with added plasminogen (3 unit/ml) at 37° C. for 1 hour. The peptide (fibrin degradation product: FDP) which was liberated into the supernatant was quantitated using an FDP-EIA kit (produced by American Diagnostics Co.).

Figure 7:
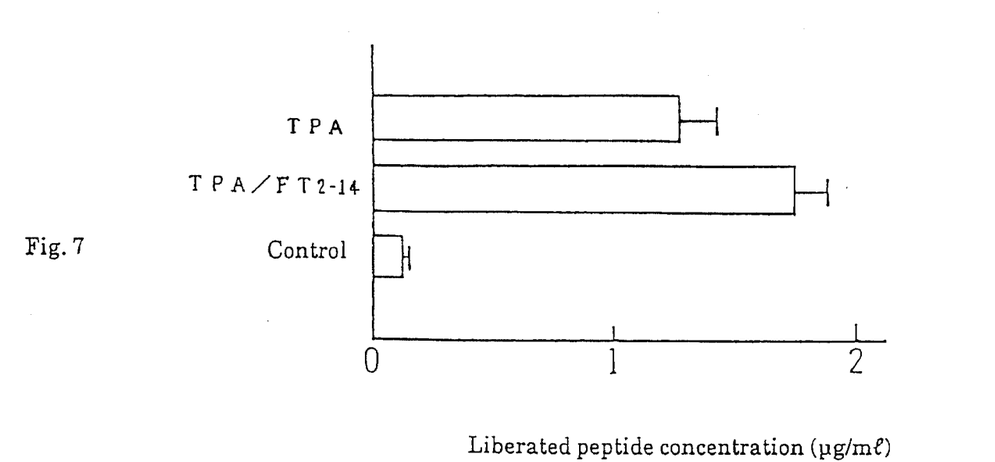
FIG. 7 shows the capability of fibrinolysis of TPA on fibrin-bound Cellulofine grains pretreated with the bi-specific antibody FT 2-14 prepared in Example 4-③ (TP-T 2-14) and on untreated fibrin-bound Cellulofine grains (TPA) (see Example 8).

The results are shown in FIG. 7.

TPA had a stronger effect on fibrin-Cellulofine grains pretreated with the bi-specific antibody FT 2-14 than on untreated fibrin-Cellulofine grains; TPA's capability of fibrinolysis was strengthened by the antibody.

Example 9

(Property① ( of anti-UK-anti-human-fibrin bi-specific antibody FU 1-74)

Figure 8:
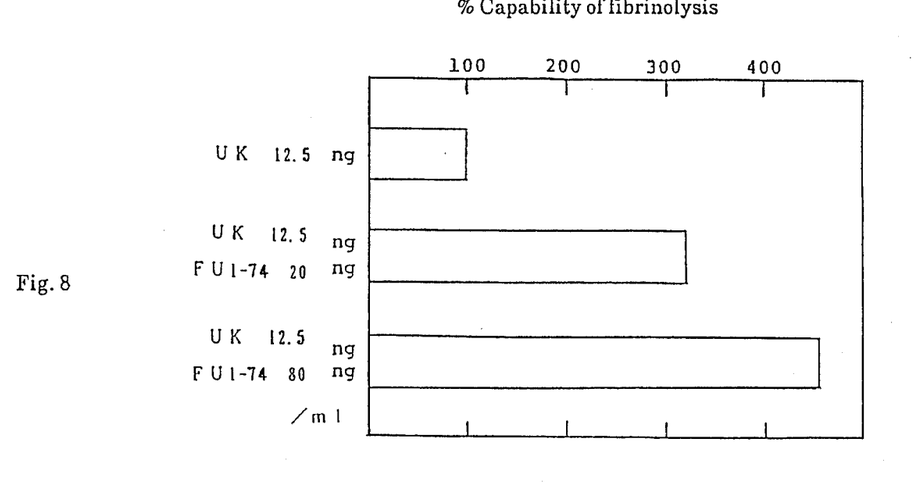
FIG. 8 shows the capability of fibrinolysis of simple UK and the immunocomplex of UK and the bi-specific antibody FU 1-74 prepared in Example 5-③ (see Example 9).

Both 2.5 μl of a UK solution (25 ng/ml) and a solution (40 ng/ml or 160 ng/ml) of the bi-specific antibody FU 1-74 obtained in Example 5-③ were injected into one well of the fibrin-agarose plate described in Reference Example 6, followed by reaction at 37° C. for 4 hours. Then, the resulting fibrinolysis plaque was measured and compared with the fibrinolysis plaque obtained with unconjugated UK. The results are shown in FIG. 8. In comparison with unconjugated UK, the coexistence of FU 1-74 antibody caused an increase of 3 to 5 times in the capability of fibrinolysis.

Example 10

(Enhancement of in vitro fibrinolytic capability of anti-TPA anti-human-fibrin bispecific antibody FT2-14 and anti-UK anti-human-fibrin bispecific antibody FU1-74)

Figure 9:
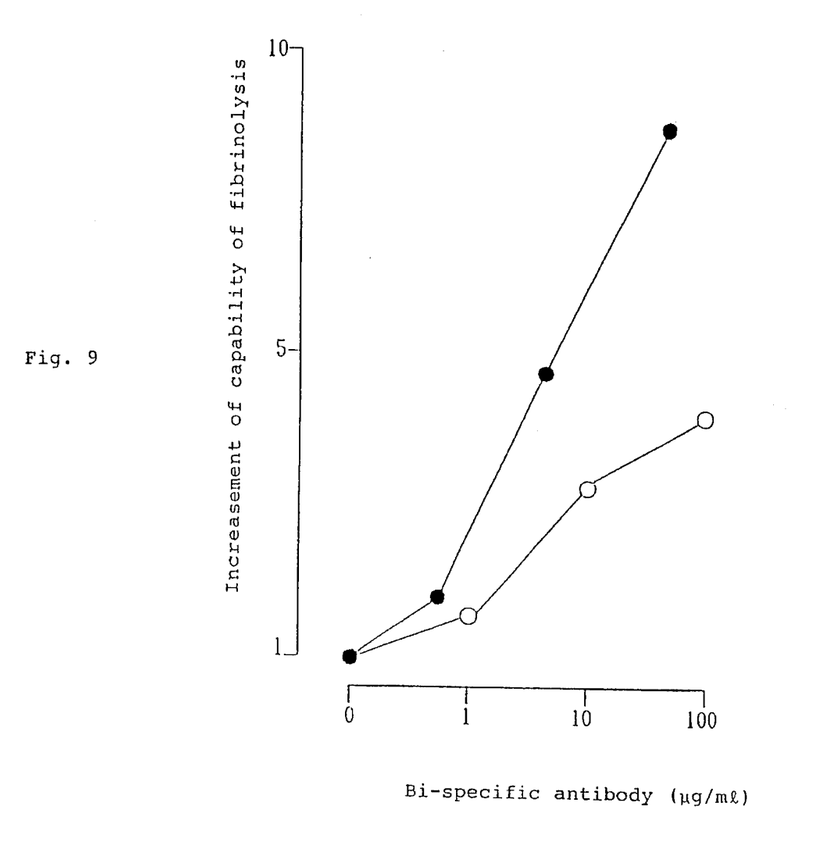
FIG. 9 shows the fibrinolytic capability obtained when using TPA alone or TPA and FT 2-14, the bispecific antibody prepared in Example 4-③, in combination (○), and the fibrinolytic capability obtained when using UK alone or UK and FU 1-74, the bispecific antibody prepared in Example 5-③, in combination (●) (see Example 10).

Columns packed with fibrin-Cellulofine grains obtained in Example 8 were respectively coupled with FT2-14 (0 to 100 μg/ml) obtained in Example 4-③ and FU1-74 (0 to 50 μg/ml) obtained in Example 5- ③ and then washed with PBS containing 0.01% Triton X-100 (PBS-T). A TPA solution was injected to the FT2-14-treated columns and a UK solution to the FU1-74-treated columns at 200 μg/400 ml a washings with PBS-T, the carrier Cellulofine grains were transferred to test tubes and reacted with added plasminogen (4.5 units/1.5 ml) at 37° C. for 2 hours. After addition of an equal amount of 6 mM para-amidinophenyl methanesulfonylfluoride, Fibrin Degradation Products (FDP) liberated from the Cellulofine grains were measured using an EIA kit (produced by American Diagnostica Co.). The results are shown in FIG. 9. Enhancement of fibrinolytic capability by 3.8 times was noted in the 100 μg/ml FT2-14 treated fibrin-Cellulofine grains (○) and enhancement by 8.5 times in the 50 μg/ml FU1-74-treated fibrin-Cellulofine grains (●), in comparison with the fibrinolytic capability of TPA (○) and UK (●) on fibrin-Cellulofine grains not treated With antibody.

Example 11

(Enhancement of in vivo thrombolytic capability of anti-TPA anti-human-fibrin bispecific antibody FT2-14)

① Preparation of rabbit jugular vein thrombus model

After anesthesia of male rabbits (2.5 to 3.5 kg) by intraperitoneal injection of pentobarbital (90mg/1.5 ml/rabbit) and urethane (1.5 mg/3 ml/rabbit), a blood sampling cannula was inserted to the right femoral vein and a blood injecting cannula and a piece of woolen thread to the left jugular vein. The jugular vein was clipped to block blood flow in a portion of about 3 cm in width, and this was followed by vessel inside washing with sequential addition of physiological saline and then 0.2 ml of a 12mM $CaC_{12}$ solution containing 10 U/ml thrombin. To the washed vessel was injected 0.2 ml of autoblood collected via the femoral vein. The cannulae were immediately removed; the resulting openings were ligated. The animal was then kept standing for 30 minutes to allow blood to coagulate.

② Injection of subject drug solution

Figure 10:
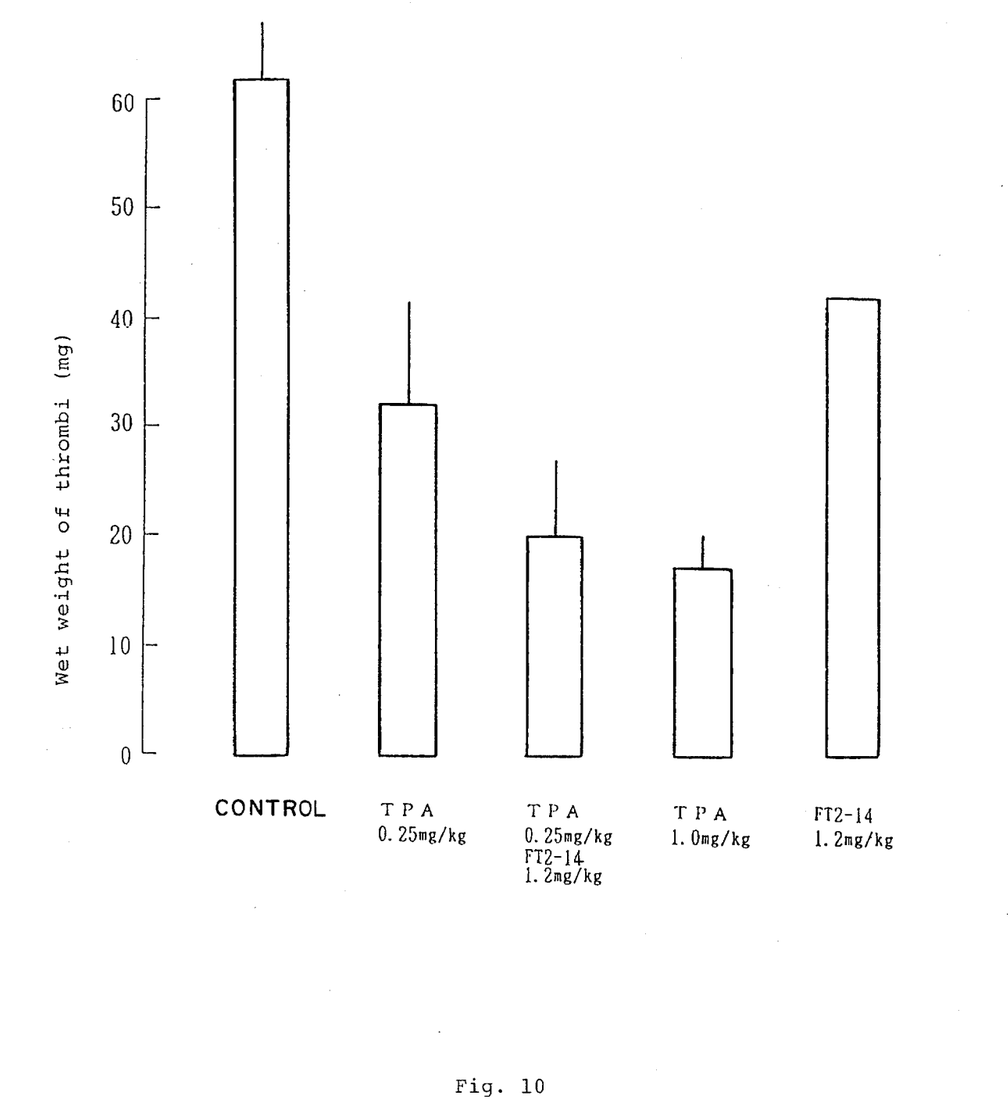
FIG. 10 shows the results of enhancement of the thrombolytic capability of TPA by FT 2-14, the bispecific antibody prepared in Example 4-③, in the rabbit jugular vein thrombus model (see Example 11).

Heparin was intraperitoneally (250 U/kg) and subcutaneously (500 U/kg) injected to the thrombus model rabbits; the clip was removed from the jugular vein. An injection needle was then inserted to the ear vein on the opposite side, and this was followed by intravenous injection of a subject drug solution in an mount of 10% of the entire dose volume at 2 ml/rabbit and then continuous injection of the remaining 90% volume at a flow rate of 6 ml/hour over a period of 4 hours. Four hours later, the thrombus adhered to the woolen thread was taken out and weighed on a wet basis. The subject drug solutions used were a control physiological saline, TPA solutions (0.25 mg/kg and 1.0mg/kg), the FT2-14 antibody solution (1.2mg/kg) and TPA/FT2-14 antibody complex solution (0.25 mg/kg TPA+1.2 mg/kg FT2-14) obtained in Example 4-③. The results are shown in FIG. 10.

When 0.25 mg/kg TPA was continuously injected over a period of 4 hours, the wet weight of thrombus decreased from 61.5 ±7.2mg (n=4) in the control group to 31.7 ±10.1 mg (n=6). In the group receiving 0.25 mg/kg TPA and 1.2 mg/kg FT2-14 in combination in a molar ratio of 1 of TPA to 2 of the bispecific antibody (bs AB), the wet weight became 19.6±6.5 mg (n=7), i.e., the thrombolytic capability was enhanced to the extent that it was almost equal to the wet weight of thrombus in the 1.0mg/kg TPA group, 15.5±3.5 mg (n=3). In the 1.2mg/kg FT2-14 group, the wet weight of thrombus was 41.5 mg (n=1).

Example 12

(Preparation of hybridoma which produces mouse anti-low-molecular-weight-UK monoclonal antibody)

① Immunization

Mouse immunization was conducted in exactly the same manner as in Example 2-① but commercially available two-chain low molecular weight UK (available from JCR Co.; Code No. 300110; molecular weight: 33,000) was used in place of the TPA described in Example 2-①.

② Cell fusion

Cell fusion was conducted in accordance with the method described in Example 1-③.

③ Hybridoma selection and cloning

Hybridomas were screened by the EIA procedure described in Reference Example 10 using a microplate bound with low molecular weight UK and subjected to the same procedure as Example 1-④ to obtain hybridomas which produce anti-low-molecular-weight-UK MoAb. Out of these hybridomas, mouse hybridoma UK 1-6 was selected, which produces an anti-low-molecular-weight-UK MoAb which specifically binds to UK without impairing the fibrinolytic capability of UK. The immunoglobulin class and subclass of the antibody UK 1-6 produced by the hybridoma thus obtained were identified as IgG₁ (k chain) by the Ouchterlony's method.

Example 13

(Production ② of hybrid monoclonal antibody possessing anti-UK anti-human-fibrin bispecificity)

① Cell fusion

FIB 1-11, the hybridoma which produces anti-human-fibrin antibody and which was obtained in Example 1, and UK 1-6, the hybridoma which produces anti-low-molecular-weight-UK antibody and which was obtained in Example 12, were subjected to fluorescent staining respectively with FITC and TRITC in accordance with the method described in Example 4-①, and then subjected to cell fusion using PEG 6000. The cells were then applied to FACS to select double-stained cells, which were cultivated.

② Hybrid hybridoma selection and cloning

The culture supernatants obtained from the wells in which cell proliferation occurred 1 to 2 weeks after cell fusion were each subjected to the EIA procedure described in Reference Examples 1, 9 and 10 to determine their antibody activity.

The well which showed maximum hybrid antibody activity was subjected to cloning by limiting dilution method, and the desired mouse hybrid hybridoma FU 2-16, which produces bispecific antibody, was obtained.

Figure 11:
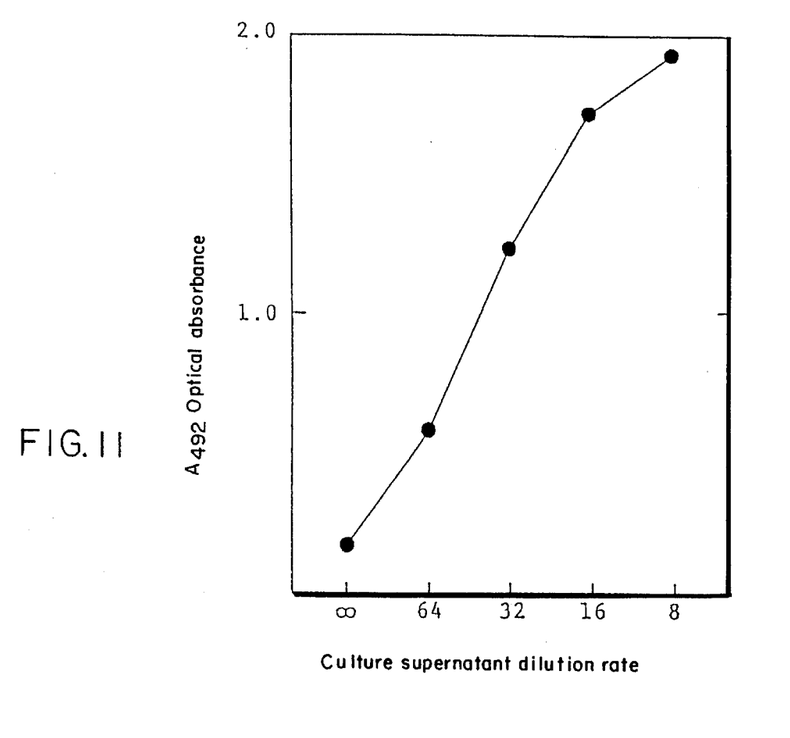
FIG. 11 shows the dilution curve of the culture supernatant of FU 2-16, the mouse hybrid hybridoma which produces anti-UK anti-human-fibrin bispecific antibody and which was prepared in Example 13 (see Example 13).
Figure 12A:
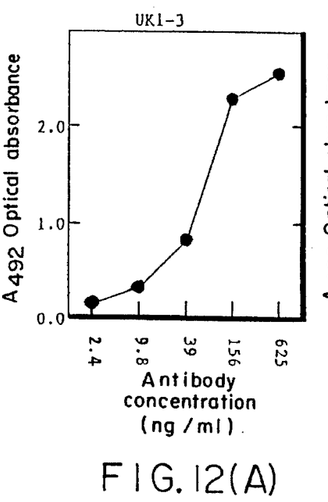
Figure 12B:
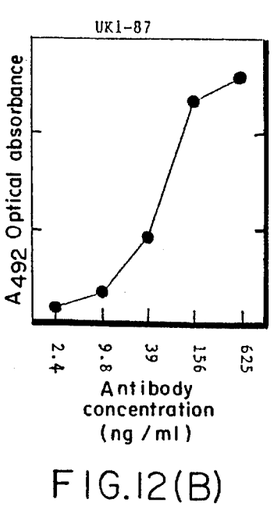
Figure 12C:
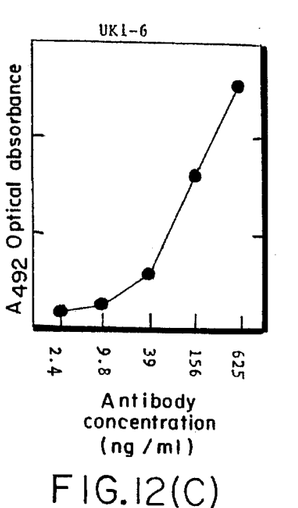
Figure 12D:
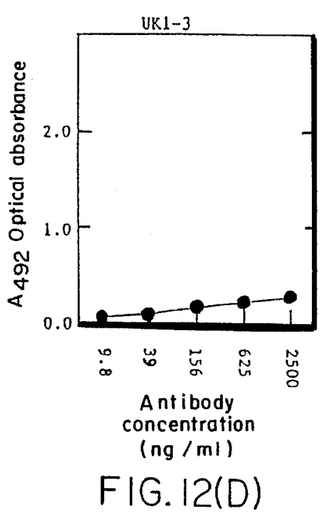
Figure 12E:
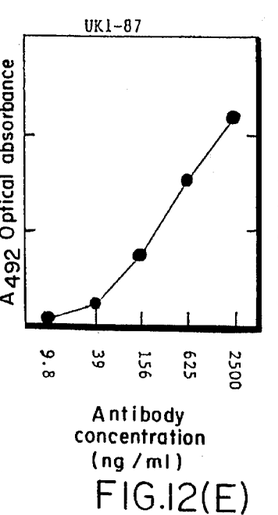
Figure 12F:
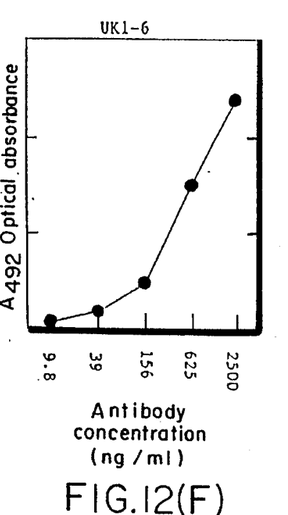

The culture supernatant of the hybrid hybridoma FU 2-16 was assayed by the EIA procedure described in Reference Example 5. The results are shown in FIG. 11.

③ Purification of hybrid antibody

Ascites fluid was collected by the method described in Example 4-③ and subjected to ammonium sulfate salting-out and immunoaffinity chromatography using a fibrin-coupled column and a UK-coupled column to yield about 23 mg of FU 2-6, the anti-UK anti-human-fibrin b/specific anti-body of the present invention, from about 20 ml ascites fluid.

Example 14

(Property① of anti-UK monoclonal antibody)

UK 1-3, 1-87 and 1-6, the anti-UK monoclonal antibodies obtained in Examples 3 and 12, were subjected to the EIA procedures respectively using a UK-bound microplate and a low molecular weight UK-bound microplate (described in Reference Examples 3 and 10, respectively), and were compared as to avidity to UK [FIG. 12 (A)] and to low molecular weight UK [FIG. 12 (B)]. The results are shown in FIG. 12.

UK 1-3 antibody did not bind to low molecular weight UK, while UK 1and UK 1-6 antibodies both showed equivalent reactivity to UK and low molecular weight UK.

Example 15.

(Property② of anti-UK monoclonal antibody)

Figure 13A:
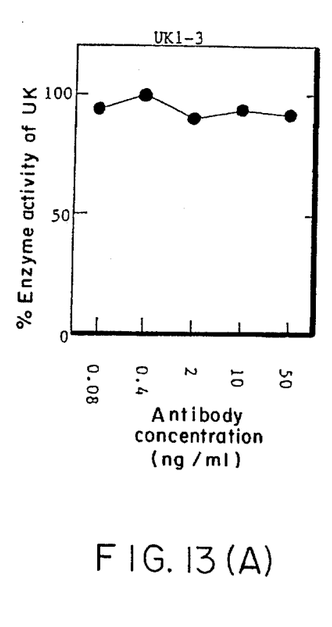
Figure 13B:
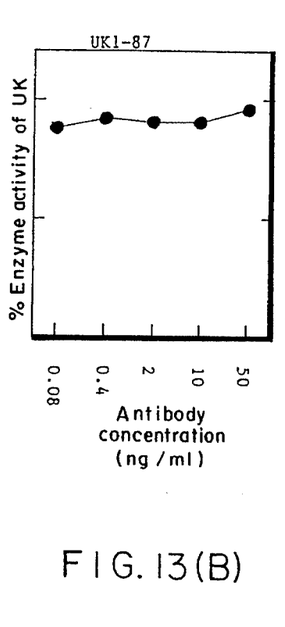
Figure 13C:
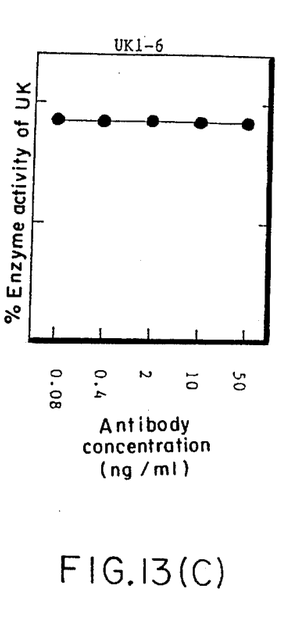

Anti-UK monoclonal antibodies UK 1-3, 1-87 and 1-6 obtained in Examples 3 and 12 were subjected to a UK enzyme activity neutralization test using synthetic peptide substrate S-2444 described in Reference Example 11. The results are shown in FIG. 13.

None of these anti-UK monoclonal antibodies inhibited UK enzyme activity.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Hybrid monoclonal antibody FU1-74 produced by hybrid hybridoma FERM BP-2334.

2. The antibody of claim 1, wherein the antibody is a F(ab')₂ fragment.

3. Mouse hybrid hybridoma FU1-74 deposited as FERM BP-2334.

\* \* \* \* \*